United States Patent [19]

Smith et al.

[11] 4,081,453
[45] Mar. 28, 1978

[54] CERTAIN 3,5-DIHALO-1,2,4-THIADIAZOLE PREPARATIONS

[75] Inventors: Gary L. Smith, Lewisburg; Dennis Eugene Reese, Marysville, both of Ohio

[73] Assignee: The O. M. Scott & Sons Company, Marysville, Ohio

[21] Appl. No.: 348,044

[22] Filed: Apr. 5, 1973

Related U.S. Application Data

[63] Continuation-in-part of Ser. No. 198,399, Nov. 12, 1971, abandoned.

[51] Int. Cl.² ............................................ C07D 285/08

[52] U.S. Cl. ................................. 260/302 D; 71/90; 260/302 SD; 424/270

[58] Field of Search .................................... 260/302 D

[56] References Cited

U.S. PATENT DOCUMENTS

3,090,721   5/1963   Uhlonbrock et al. ........... 260/302 D

*Primary Examiner*—R. Gallagher
*Attorney, Agent, or Firm*—Strauch, Nolan, Neale, Nies & Kurz

[57] ABSTRACT

3,5-Dihalo-1,2,4-thiadiazoles and their preparation from corresponding 5 alkylthio compounds, useful as intermediates for fumigants are disclosed.

6 Claims, No Drawings

CERTAIN 3,5-DIHALO-1,2,4-THIADIAZOLE PREPARATIONS

This application is a continuation-in-part of Application Ser. No. 198,399 filed Nov. 12, 1971 and now abandoned.

The present invention relates to thiadiazoles and, more particularly, to 1,2,4-thiadiazoles of the formula

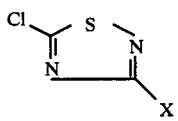     (I)

were X is bromine or chlorine.

The foregoing compounds can be converted in high yields to a variety of 5-substituted - 3-halo-1,2,4-thiadiazoles having pesticidal and other biological activity. One class of such compounds which can be made from the formula (I) intermediates consists of those having the formula

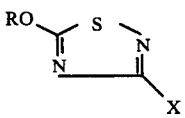     (Ia)

Examples of formula (Ia) compounds and the intermediate from which they were prepared are shown in the following tabulation:

| NAME OF COMPOUND - | INTERMEDIATE[1] |
|---|---|
| FORMULA (Ia) | |
| 3-Chloro-5-methoxy-1,2,4-thiadiazole | a (R=CH$_3$—) |
| 3-Bromo-5-ethoxy-1,2,4-thiadiazole | b (R=CH$_3$CH$_2$—) |
| 3-Chloro-5-(n-butoxy)-1,2,4-thiadiazole | a (R=CH$_3$(CH$_2$)$_{3-}$) |
| 3-Bromo-5-(n-butoxy)-1,2,4-thiadiazole | b (R=CH$_3$(CH$_2$)$_3$—) |

[1]"a" is the compound of Formula (Ia) where X is chloro and "b" is the compound of the same formula where X is bromo.

1. "a" is the compound of Formula (Ia) where X is chloro and "b" is the compound of the same formula where X is bromo.

The foregoing compounds and others of formula (Ia) possess a high degree of biological growth regulating activity in the vapor phase and are accordingly valuable as fumigants. In tests as fumigants on *Lactuca sativa* (lettuce), *Lolium perenne* (ryegrass), *Cichorium intybus* (chickory), and *Lepidium virginicum* (peppergrass), the listed formula I(a) compounds produced kills of from 90 to 100 percent.

Compounds of formula I(a) are also pre-emergence herbicides.

The procedures by which the intermediates of Formula I are converted to the compounds of Formula I(a) are as follows:

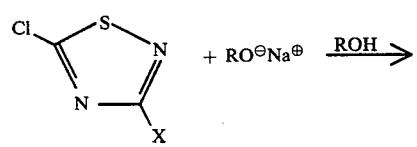

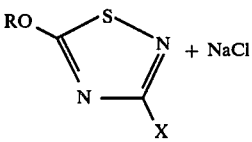

where X = bromine or chlorine.

A reaction vessel is charged with the 3-halo-5 chloro-1,2,4-thiadiazole intermediate (0.015 mole) and 10 ml. of the requisite alcohol. Freshly prepared sodium alkoxide (0.015 mole) dissolved in 10 ml. of alcohol is added dropwise to this with rapid stirring under a nitrogen atmosphere.

After the addition of the alcohol is completed, the slurry which results is allowed to stir for an additional 30 minutes to ensure complete reaction. The solid (NaCl) is removed by filtration and the resulting filtrate concentrated in vacuo. This residue is slurried in 50 ml. of diethyl ether, filtered to remove the remaining inorganic salt and finally reconcentrated in vacuo to give the desired derivative. Vacuum distillation or recrystallization gives high purity final products.

One of the two compounds covered by formula I above is 3-bromo-5-chloro-1,2,4-thiadiazole,

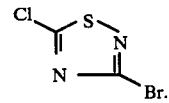

So far as we are aware, this is a novel compound; and we are the first to discover a method for preparing it.

The other of the compounds of formula (I) is 3,5-dichloro-1,2,4-thiadiazole,

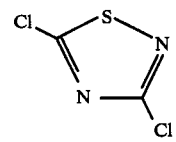

The preparation of this compound is reported by Goerdler and Tom in *Halogenthiodiazole durch Chlorolyse einiger Schwefelhaltiger Verbindungen*, Chem. Berichte, 98 1544–1555 (1965). Goerdler discloses the following methods for making this compound:

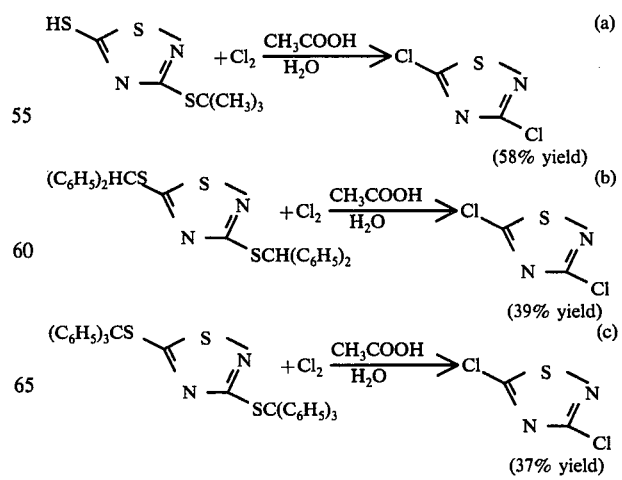

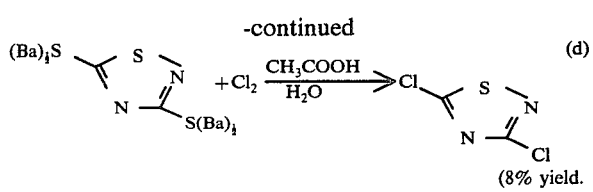

(8% yield.)

As is apparent from the foregoing, the yields of 3,5-dichloro-1,2,4-thiadiazole obtained by Goerdler's syntheses are at best low (we have been unable to achieve yields as high as the reported 58% following his route (a).

We have now discovered a novel, improved method of making the dichloro compound in yields of 85–90% with nearly 100% purity. Furthermore, this method can be used to prepare 3-bromo-5-chloro-1,2,4-thiadiazole, while Goerdler's cannot. Among the other advantages of this novel process are (a) the reactants are inexpensive; and (b) the synthesis times are short.

Our novel method proceeds as follows:

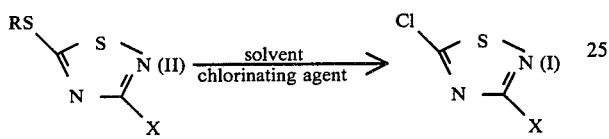

where R is $C_1$–$C_4$ alkyl or benzyl, and X is chlorine or bromine.

The preferred solvent is a mixture of on the order of ten parts of acetic acid to one part of water. Other solvent systems such as glacial acetic acid and wet chloroform may be employed instead although longer reaction times and/or higher temperatures may be necessary.

The preferred chlorinating agent is chlorine gas because of the high yields obtained when it is used. However, other active chlorinating agents can be employed if desired, should lower yields be acceptable. Examples of such agents are sulfuryl chloride and triphenyl phosphine chloride.

The reaction is initially exothermic; and, if the preferred solvent systems and chlorinating agent are employed, 80% yields can be obtained without the application of heat. For maximum yields, however, it is preferred that the reaction be heated as needed to keep it at a temperature of ca. 60° C. for one-two hours (or even longer if other than the preferred solvent system and chlorinating agent are employed).

The starting compounds of formula II may be prepared by the method disclosed in copending Application No. 803,411 (now U.S. Pat. No. 3,736,328); that is, by the oxidative halogenation of compounds of the formula

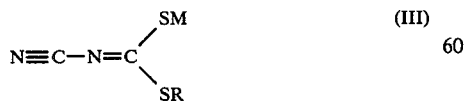

where R is $C_1$–$C_4$ alkyl or benzyl and M is an alkali or alkaline earth metal according to the following reaction:

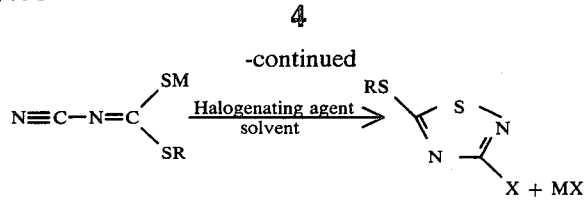

where R, M, and X are all as aforesaid.

The compounds of Formula III and their preparation are described in commonly assigned, Timmons et al Application No. 834,510 filed June 18, 1969 (now U.S. Pat. No. 3,658,901), which is hereby also incorporated by reference herein.

Elemental chlorine and bromine, surfuryl and thionyl chlorides, trichloromethane sulfenyl chloride, and phosphorus pentachloride are examples of suitable halogenating agents for the reaction diagrammed above; chloroform and water are suitable reaction media. The reactants will typically be stirred first at 0 to −5° C, then at room temperature, and finally at reflux or first at 0 to −5° C. and then at reflux. Maximum yields are typically obtained by employing total reaction times of 3 to 24 or more hours.

In conjunction with the foregoing, we have developed a novel, inexpensive procedure for cleaning up the 5-methylthio starting materials of formula II made by the procedure just described before they are converted to the compounds of formula I. It is because of this that the desired products are obtained in essentially pure form without clean-up in our novel process. This is, of course, of considerable importance from an economic point-of-view.

In view of the at least general similarity between the reaction involved in converting the compounds of formula III to those of formula II and in converting the latter to the compounds of formula I, we have attempted to go directly from compounds of formula III to the dichloro compound of formula I without isolating the 1,2,4-thiadiazole intermediates of formula II. The desired product was obtained, but only in low yields (31% from potassium methyl cyanodithioimidocarbonate and 24% from the sodium analog).

We have also attempted to convert the following compounds, which structurally resemble those of formula II, to the dichloro compound of formula I by reacting them with chlorine gas at elevated temperature:

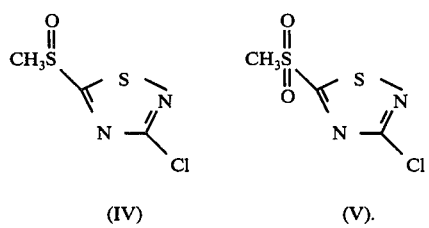

A very low, 21%, yield of the desired product was obtained from the sulfinyl compound of formula IV; the sulfonyl compound of formula V did not react to produce the desired product.

Also, in this regard, Thaler et al, "The Synethesis and Some Reactions of 1,2,4-Thiadiazolylsulfenyl Chlorides," J. Org. Chem., 36 14–18 (1971), describes the preparation of the following compounds

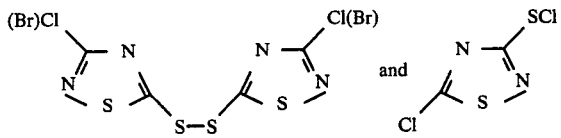

We have found that these compounds can be converted to compounds of formula I. Again, however, yields are too low (30% for the dichlorodisulfide compound and even lower for the other two) to make the synthesis route using these compounds of much practical interest.

From the foregoing, it will be apparent that one important object of the present inventon resides in the provision of the novel compound of the formula

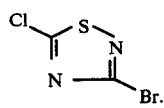

Another important and primary object of our invention resides in the provision of novel methods for making the compound identified in the preceding object in high yields with high purity.

Still another important and primary object of the invention resides in the provision of novel, improved methods for making the compound of the formula

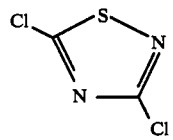

which are characterized by high yields and high purity.

Yet other important objects of the present invention will be readily apparent to those skilled in the relevant arts from this specification as will other advantages and novel features of our invention.

The following examples depict in more detail the preparation of representative compounds of formula I in accord with the principles of the present invention as well as our novel clean-up procedure for the compounds of formula II.

EXAMPLE I

Preparation of 3-chloro-5-methylthio-1,2,4-thiadiazole

The crude compound was prepared following the method described in Application No. 803,411 (now U.S. Pat. No. 3,736,328) from potassium methyl cyanodithioimidocarbonate. It was then dissolved in chloroform and extracted with aqueous potassium hydroxide to pH 8.0 to remove all acid. During the base extraction NaHSO$_3$ was also added; this removed the free halogen remaining in the product. Other reducing agents including the other alkali metal and the alkaline earth hydrogen sulfites and the alkali metal sulfites may be used insted of NaHSO$_3$, if desired.

Following the base extraction, the product was dried over anhydrous sodium sulfate and concentrated in vacuo, producing an oil which solidified upon standing.

The product is sufficiently pure to be used for the preparation of the compounds of formula I without recrystallization or similar esoteric clean-up steps. The clean-up procedure is accordingly of considerable economic and practical importance.

EXAMPLE II

Preparation of 3,5-dichloro-1,2,4-thiadiazole

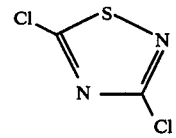

Chlorine gas was introduced to a stirred slurry of 3-chloro-5-methylthio-1,2,4-thiadiazole (166.5 g., 1.0 mole, purified as described in Example I) in 650 ml. of glacial acetic acid and 65 ml. of water. The slurry soon warmed to 70° C. and turned to a clear, light yellow solution.

The introduction of chlorine gas was continued slowly for 2 hours while maintaining the reaction mixture at 60° C.

The resulting mixture was cooled, diluted with 1800 ml. of water, and extracted with 4 × 400 ml. of chloroform. The combined chloroform extracts were washed with 20% aqueous potassium hydroxide until the water layer remained slightly basic.

The chloroform layers were then dried over anhydrous sodium sulfate; 136.9 g. (88.2% yield) of clear liquid product was recovered after atmospheric distillation. The liquid had a boiling point of 165°–167°. It was evident that a high purity product was obtained as only one peak was observed using gas chromatography analysis.

The 3,5-dichloro-1,2,4-thiadiazole prepared by this novel process was found to have the following elemental analysis:

Calculated for C$_2$Cl$_2$N$_2$S: C, 15.50; Cl, 45.75; N, 18.07; S, 20.68; Found: C, 15.70; Cl, 44.50; S, 20.88; Mass spectrum: parent peak (m/e 154).

The procedure just described was duplicated using the following compounds of formula II as starting materials and increasing the reaction time to five hours:

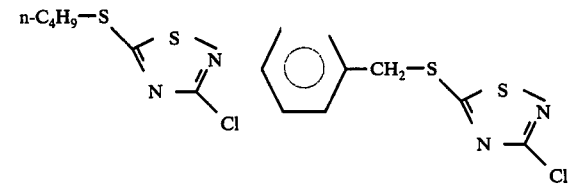

Fair-to-good yields (60% and 58.5%, respectively) of 3,5-dichloro-1,2,4-thiadiazole were obtained.

Other of the compounds of formula II can be converted to the dichloro compound of formula I in equal or better yields.

EXAMPLE III

Preparation of 3-bromo-5-chloro-1,2,4-thiadiazole

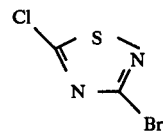

3-Bromo-5-methylthio-1,2,4-thiadiazole was prepared following the method described in Application No. 803,411; the crude product was purified using the clean-up procedure of Example I.

Chlorine gas was introduced to a stirred slurry of the purified 3-bromo-5-methylthio-1,2,4-thiadiazole (23.2 g., 0.11 mole) in 230 ml. of glacial acetic acid and 23 ml. of water. The slurry quickly warmed to 60° C. and turned to a clear, light yellow solution.

The introduction of chlorine gas was continued slowly for 2 hours while maintaining the reaction mixture at 60° C.

The mixture which resulted was cooled, diluted with 200 ml. of water, and extracted with 4 × 50 ml. of chloroform. The combined extracts were washed with aqueous 20% potassium hydroxide until the water layer remained slightly basic.

The chloroform layers were then dried over anhydrous sodium sulfate. After atmospheric distillation, 16.8 g. (76.5% yield) of clear liquid product was recovered. The liquid had a boiling point of 188°–190°. High purity of the product was established by using gas chromatography analysis; only one peak was observed.

The 3-bromo-5-chloro-1,2,4-thiadiazole prepared by this novel process was found to have the following elemental analysis:

Calculated for $C_2BrClN_2S$: C, 12.04; Br, 40.06; Cl, 17.78; N, 14.04; S, 16.08; Found: C, 12.45; Br, 39.92; N, 14.06

As was the case with the dichloro compound, the bromo compound of formula I can be prepared by using the foregoing procedure and other of the starting compounds of formula II although, again, maximum yields may in some cases be obtained by using a longer reaction time.

It will be appreciated that the instant specification and foregoing examples are set forth by way of illustration and not limitation and that various modifications and changes may be made without departing from the spirit and scope of the present invention, which is intended to be limited only by the appended claims.

What is claimed and desired to be secured by Letters Patent is:

1. The process of making a compound of the formula

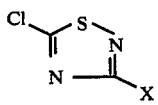

where X is chlorine or bromine by displacing RS of a compound of the formula

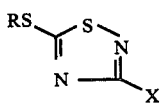

where X is as aforesaid and R is $C_1$–$C_4$ alkyl or benzyl by Cl using gaseous chlorine as a chlorinating agent.

2. The process of claim 1, wherein the reactants are maintained at a temperature of at least about 60° C. for at least 1 hour.

3. The process of claim 1, wherein the reaction is carried out in an acetic acid-water solvent system.

4. The process of making a compound of the formula

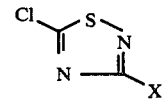

where X is chlorine or bromine by reacting a cyanodithiomidocarbonate of the formula

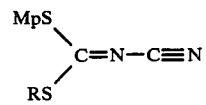

where M is an alkali or alkaline earth metal; p is 1 when M has a valence of 1 and ½ when M has a valence of 2; and R is $C_1$–$C_4$ alkyl or benzyl with a halogenting agent capable of introducing chlorine or bromine and selected from the group consisting of chlorine, bromine, thionyl chloride, trichloromethane sulfenyl chloride and phosphorus pentachloride to produce a 1,2,4-thiadiazole of the formula

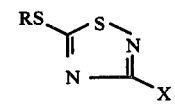

where R and X are as aforesaid; removing contaminants from the thiadiazole by the steps of dissolving said thiadiazole in a solvent, extracting the resulting solution of said thiadiazole with a base and a reducing agent selected from the group consisting of alkali metal sulfites, hydrogen sulfites, and alkaline earth metal hydrogen sulfites; and displacing RS of said thiadiazole by Cl using gaseous chlorine as a chlorinating agent to produce a compound of the formula

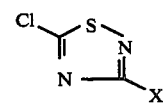

where X is as aforesaid.

5. The method of claim 4, wherein the solvent is chloroform, the base is potassium hydroxide and the reducing agent is sodium hydrogen sulfite.

6. The compound of the formula

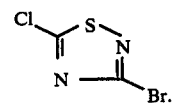

* * * * *